(12) United States Patent
Pack (10) Patent No.: US 7,792,238 B2
(45) Date of Patent: Sep. 7, 2010

(54) METHOD AND SYSTEM FOR RECONSTRUCTING CONE-BEAM PROJECTION DATA WITH REDUCED ARTIFACTS

(75) Inventor: Jed Douglas Pack, Glenville, NY (US)

(73) Assignee: General Electric Company, Niskayuna, NY (US)

(*) Notice: Subject to any disclaimer, the term of this patent is extended or adjusted under 35 U.S.C. 154(b) by 226 days.

(21) Appl. No.: 12/032,810

(22) Filed: Feb. 18, 2008

(65) Prior Publication Data
US 2009/0207964 A1 Aug. 20, 2009

(51) Int. Cl.
*A61B 6/00* (2006.01)
(52) U.S. Cl. .......................................................... 378/4
(58) Field of Classification Search ................ 378/4
See application file for complete search history.

(56) References Cited

U.S. PATENT DOCUMENTS

| | | | |
|---|---|---|---|
| 5,625,660 A * | 4/1997 | Tuy ............................. | 378/15 |
| 5,960,055 A | 9/1999 | Samarasekera et al. | |
| 5,999,587 A * | 12/1999 | Ning et al. ..................... | 378/4 |
| 6,324,247 B1 * | 11/2001 | Besson ......................... | 378/15 |
| 6,339,632 B1 * | 1/2002 | Besson ......................... | 378/15 |
| 2005/0175144 A1 | 8/2005 | Hsieh | |
| 2006/0067457 A1 | 3/2006 | Zamyatin | |
| 2006/0109952 A1 * | 5/2006 | Chen ............................ | 378/4 |
| 2006/0115040 A1 * | 6/2006 | Chen ........................... | 378/19 |
| 2006/0140338 A1 | 6/2006 | Bruder et al. | |
| 2006/0198491 A1 * | 9/2006 | Taguchi ....................... | 378/15 |
| 2006/0291611 A1 | 12/2006 | Pack et al. | |

FOREIGN PATENT DOCUMENTS

| WO | WO2004072904 | 8/2004 |
|---|---|---|
| WO | WO2006058124 | 6/2006 |
| WO | 2006073584 | 7/2006 |
| WO | 2006131872 | 12/2006 |
| WO | 2007004196 | 1/2007 |
| WO | WO2006073584 | 2/2008 |

OTHER PUBLICATIONS

Yu et al., Katsevich-type Algorithms for Variable Radius Spiral Cone-Beam CT, Proc. of SPIE, vol. 5535, 2004, pp. 550-557.*
Nett et al., Arc based cone-beam reconstruction algorithm using an equal weighting scheme, Journal of X-ray Science and Technology, 15, 2007, pp. 19-48.*
Noo, Frederic et al., "A Two-step Hilbert Transform Method for 2D Image Reconstruction", Physics in Medicine and Biology, 49, (2004) 3903-3923.

* cited by examiner

*Primary Examiner*—Edward J Glick
*Assistant Examiner*—Alexander H Taningco
(74) *Attorney, Agent, or Firm*—Jason K. Klindtworth (57) ABSTRACT

A method for generating an image of an object is provided. The method comprises acquiring projection data at one or more projection views along a circular scan trajectory and generating a corrected projection dataset based upon a weighted derivative applied to a subset of the projection data. The method further comprises backprojecting the corrected projection dataset along one or more projection rays associated with one or more of the projection views, to generate a reconstructed image of the object.

18 Claims, 10 Drawing Sheets

METHOD AND SYSTEM FOR RECONSTRUCTING CONE-BEAM PROJECTION DATA WITH REDUCED ARTIFACTS

BACKGROUND

The invention relates generally to image reconstruction and more particularly to techniques for reconstructing cone-beam projection data, with reduced cone-beam artifacts.

Most modern Computed Tomography (CT) scanners are based on a third generation architecture, which embodies a single x-ray source and a large x-ray detector. The x-ray detector can be a one-dimensional, usually curved, array of detector cells, resulting in fan-beam geometry. In axial scans (i.e. the patient table does not move during the gantry rotation) the result is a purely planar dataset to which two-dimensional ("2D") filtered backprojection (FBP) can be applied. Reconstruction is theoretically exact, and any possible image artifacts may come from physical limitations of the scanner, such as quantum noise, aliasing, beam hardening, and scattered radiation.

Since about 1990, multi-slice or multi-detector-row CT systems have become the standard CT architecture for premium medical scanners, wherein the detector has multiple rows, i.e. a two-dimensional array of detector cells, resulting in cone-beam geometry. Since these geometries do not result in planar datasets, 2D image reconstruction algorithms will not be based on the correct scan geometry and may result in cone-beam artifacts. For the axial scan mode, Feldkamp, Davis, and Kress proposed a three-dimensional ("3D") cone-beam reconstruction algorithm ("FDK algorithm") that adapts 2D fan-beam filtered backprojection (FBP) to cone-beam geometry. The FDK algorithm works well near the mid-plane and near the center of rotation, but artifacts occur and get worse as the cone-angle increases. For 40 mm-coverage scanners (which typically corresponds to about a 4 degree cone-angle) significant artifacts occur, particularly towards the z=-20 mm and z=20 mm slices. The raw CT data is actually fundamentally incomplete in 3D axial scans, and therefore, even the best thinkable algorithm will result in artifacts in some cases.

On the other hand, in helical cone-beam scans, the data is fundamentally complete (provided the table speed is not too high compared to the gantry rotation speed and the slice thickness) and therefore exact reconstruction is possible. The FDK algorithm has been adapted for helical scan modes, but results in non-exact or approximate reconstruction. Accordingly, exact 3D helical cone-beam reconstruction algorithms (including the Katsevitch algorithm) have been developed, which perform filtering operations along special filter lines followed by backprojection.

Exact reconstruction techniques, while enabling the accurate reconstruction of a three-dimensional image from two-dimensional projection data with reduced cone-beam artifacts, are generally applicable only to specific types of source trajectories such as, for example, helix, saddles, variable pitch helix and circle plus arc trajectories. However, although exact reconstruction techniques exist for many trajectories including the helix, approximate algorithms are often used in practice since these algorithms provide advantages such as reduced noise, improved noise uniformity, improved spatial resolution, computational efficiency, and/or resistance to motion artifacts. In addition, for circular scan or circular segment trajectories, where certain well known criteria, such as, for example, Tuy's data completeness condition is not satisfied everywhere in the imaging volume, the data acquired along these trajectories used to reconstruct the image data, often results in cone-beam artifacts. In addition, these cone-beam artifacts are typically much more severe for reconstructions that use less than a full scan of data, not necessarily only due to the fact that data is missing, but even because of the fact that the available data is mishandled.

It would be desirable to develop techniques for reconstructing cone-beam projection data acquired along circular scan trajectories and helical trajectories, with reduced cone-beam artifacts. In addition, it would be desirable to develop techniques for reconstructing cone-beam projection data acquired along circular scan trajectories and helical trajectories, while still achieving desired image quality characteristics, such as, high computational efficiency, good dose usage and resistance to motion artifacts.

BRIEF DESCRIPTION

Embodiments of the present invention address these and other needs. In one embodiment, a method for generating an image of an object is provided. The method comprises acquiring projection data at one or more projection views along a circular scan trajectory and generating a corrected projection dataset based upon a weighted derivative applied to a subset of the projection data. The method further comprises backprojecting the corrected projection dataset along one or more projection rays associated with one or more of the projection views, to generate a reconstructed image of the object.

In another embodiment, a method for generating an image of an object is provided. The method comprises acquiring projection data at one or more projection views along a helical scan trajectory. The method then comprises processing the projection data to generate at least one of a ramp filtered projection dataset and a correction term and computing a corrected data value for a voxel. The corrected data value for each voxel is computed based on weighting one or more projection data values comprising the ramp filtered projection dataset and the correction term by at least one of a standard weight factor or a correction weight factor. The method further comprises performing a backprojection of the corrected data value computed for the voxel to generate a reconstructed image of the object, wherein the step of computing the corrected data value and the step of performing the backprojection is repeated for each voxel and along each projection view, to generate the reconstructed image of the object.

In yet another embodiment, a computed tomography system for generating an image of an object is provided. The system comprises an x-ray source configured to project an x-ray beam from a plurality of positions through the object and a detector configured to produce a plurality of electrical signals corresponding to the x-ray beam. The system further comprises a processor configured to process the plurality of electrical signals to generate projection data. The processor is further configured to generate a corrected projection dataset based upon a weighted derivative applied a subset of the projection data and backproject the corrected projection dataset along one or more projection rays associated with one or more of the projection views, to generate a reconstructed image of the object. Further, in one embodiment, the projection data is acquired along a circular scan trajectory along one or more projection views.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments of the present invention disclose techniques for reconstructing cone-beam projection data with reduced cone-beam artifacts. In one embodiment of the present invention, a technique for reconstructing cone-beam projection data acquired along a circular trajectory is provided. As will be appreciated by those skilled in the art, one technique for reconstructing cone-beam projection data acquired along a circular-scan trajectory is to filter the cone-beam projection data in a direction that is tangent to the path of the x-ray source and then backproject it over a super-short scan range for each voxel in the image volume. The filtered cone-beam projection data may be weighted by one if the corresponding ray is at an angle between 0 and 180 degrees and weighted by zero otherwise. However, the above technique results in a discontinuous voxel weight, wherein the weights are discontinuous at view angles 0 and 180. This characteristic is particularly not desirable in cases such as cardiac imaging where a degree of object motion is usually involved.

Figure 1:
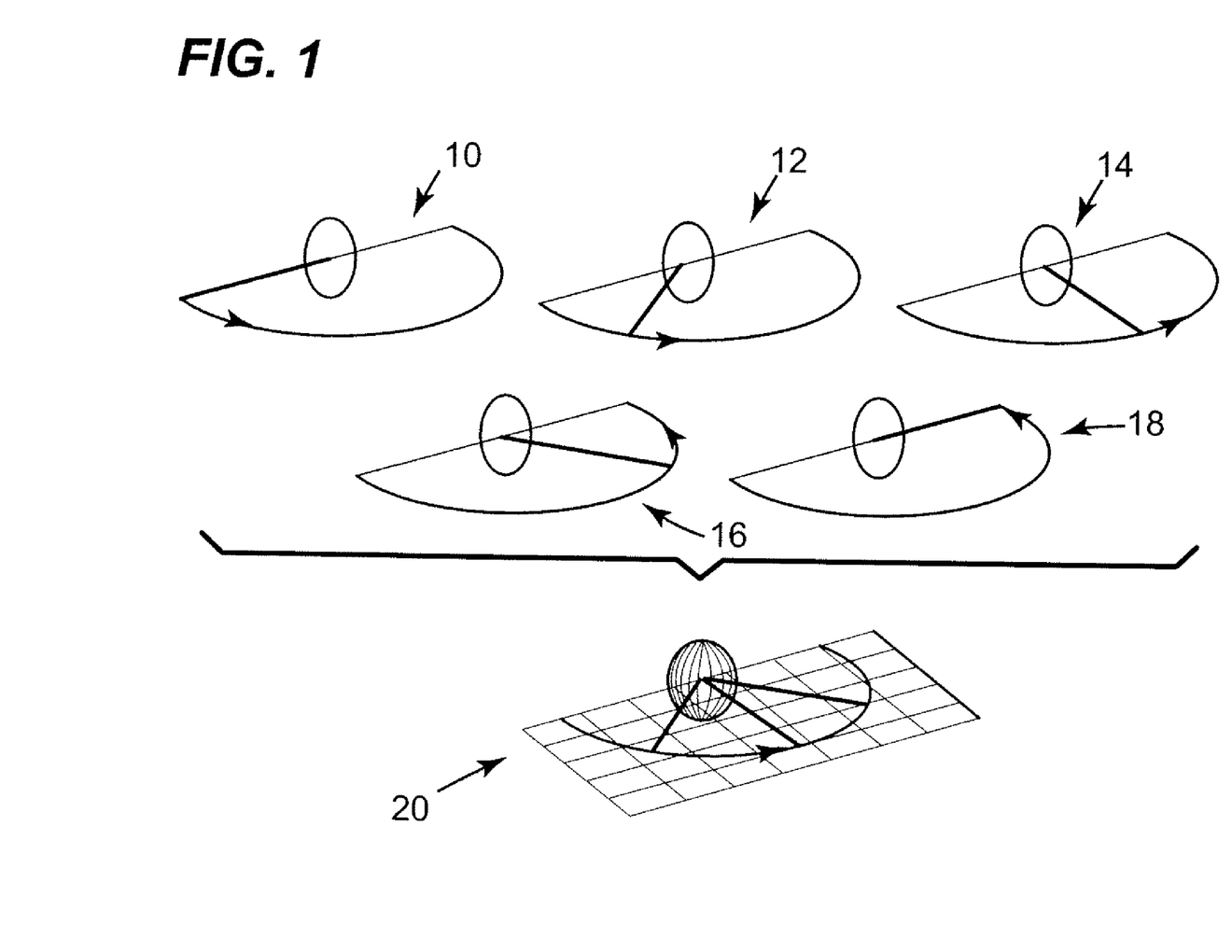
FIG. 1 is an illustration of the Radon data coverage for a reconstruction point in the plane of a super-short-circular scan x-ray source path segment.
Figure 2:
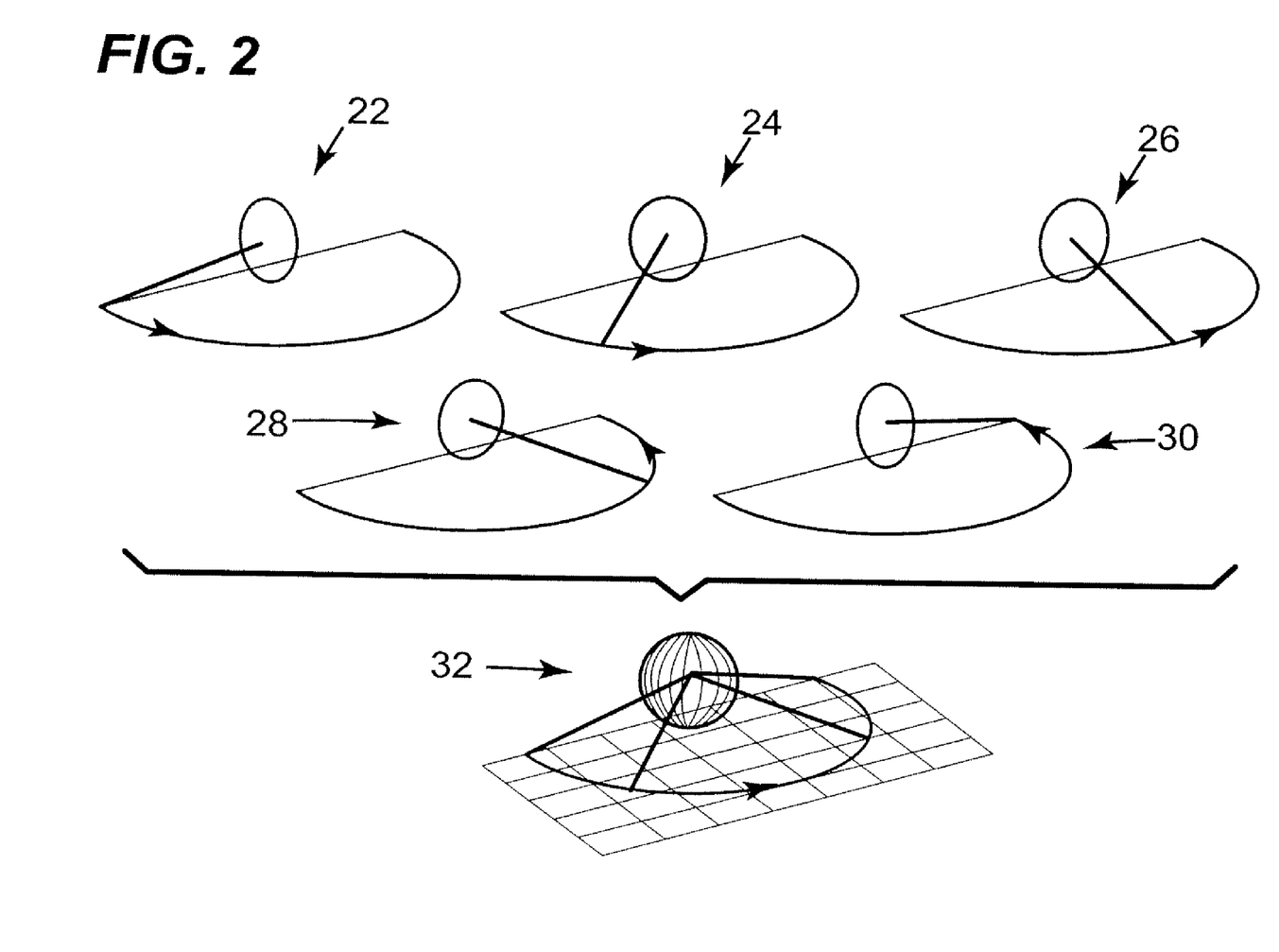
FIG. 2 is an illustration of the Radon data coverage for a reconstruction point that lies outside the plane of a super-short-circular scan x-ray source path segment.

A typical Radon data coverage for a reconstruction point in the plane of a super-short-circular scan x-ray source path segment is illustrated in FIG. 1. FIG. 1 also illustrates a plurality of points along the super-short-circular scan path and the corresponding planes of Radon (Fourier) data that are acquired at each data point. As may be observed, each of the five representative views 10, 12, 14, 16 and 18 shown in FIG. 1 provides access to the Radon (Fourier) data on the plane that is orthogonal to the ray that extends from the x-ray source point to the reconstruction point. Representative view 20 illustrates the Radon coverage for a reconstructed point in the image volume. It may also be observed that the super-short-circular-scan source path segment shown in FIG. 1 covers every radon direction exactly once (for a given reconstruction point) during a 180-degree rotation provided that the reconstruction point lies in the plane of the x-ray source trajectory. However, and as illustrated in FIG. 2, when the reconstruction point lies outside the plane of the x-ray source trajectory, it is offset in the z-direction, as shown by the five representative views, 22, 24, 26, 28 and 30 in FIG. 2. Representative view 32 illustrates the Radon coverage for a reconstructed point in the image volume that is offset in the z-direction.

Figure 3:
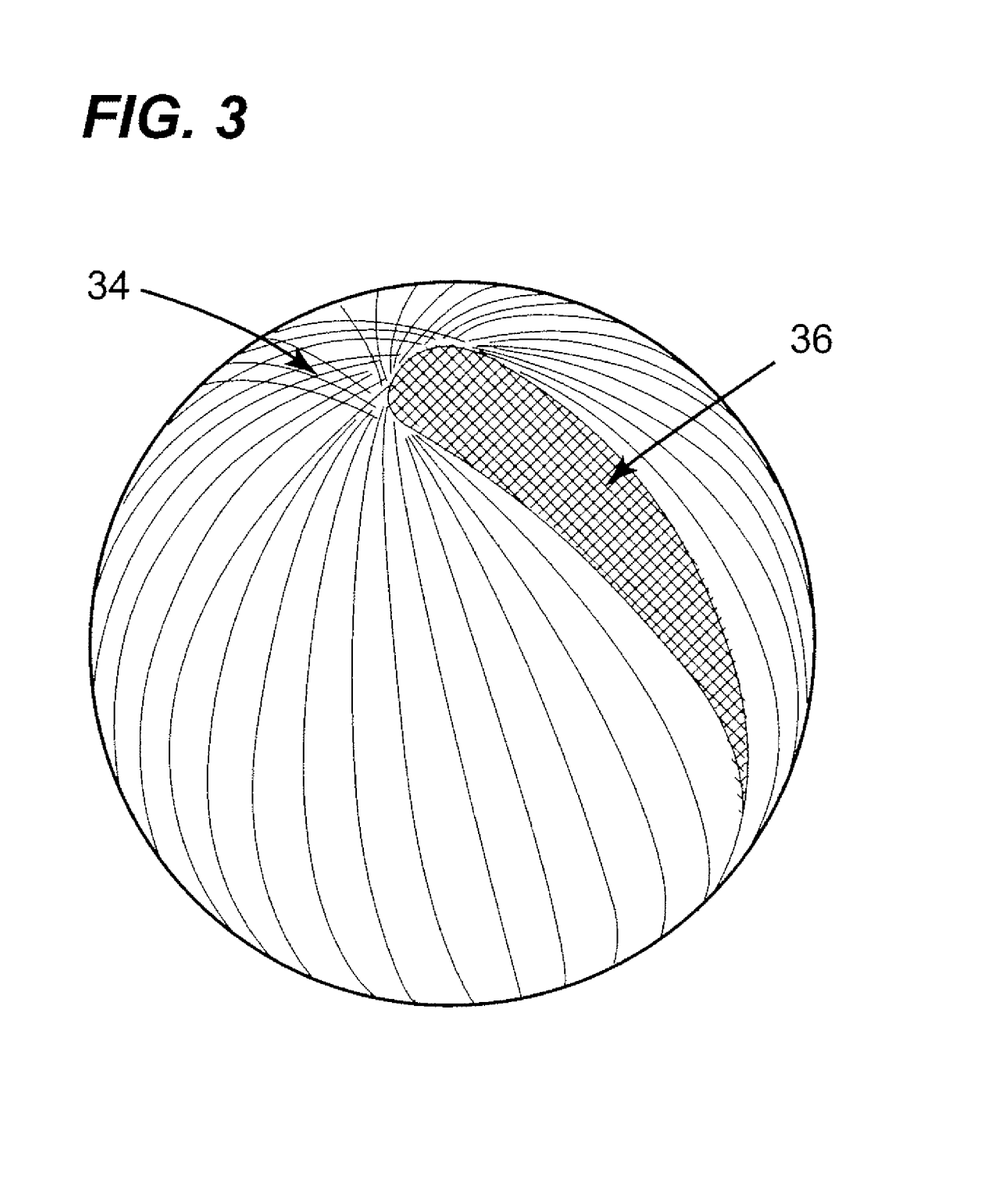
FIG. 3 is an illustration of the Radon data coverage for a reconstruction point shown in FIG. 2, in greater detail.

FIG. 3 illustrates the Radon data coverage for a reconstruction point shown in FIG. 2, in greater detail. Since the filtering operation is applied along the direction that is tangent to the path, data corresponding to a given direction is weighted by one each time it is measured. However, for points that do not lie in the plane of the x-ray source path, such as, as illustrated in FIG. 2, there are certain directions that are measured twice and certain directions that are not measured at all, thereby creating a wedge of radon data that is either missing or redundantly measured for a given reconstruction point in the reconstructed image volume. The wedge of data corresponds to regions of radon data, generated by data points in the radon (Fourier) space that are covered twice or not covered at all. Referring to FIG. 3, a data wedge is formed between the regions labeled 34 and 36, wherein data points in the region 34 are covered twice as the x-ray source moves along the segment of the circular scan trajectory and wherein data points in the region 36 are not covered at all. Furthermore, it is to be appreciated that the wedge of data that is given an incorrect weight is typically much larger than the cone of data that is unavailable from a full scan acquisition, or even the cone-like region that is missing from a less than full scan acquisition.

Figure 4A:
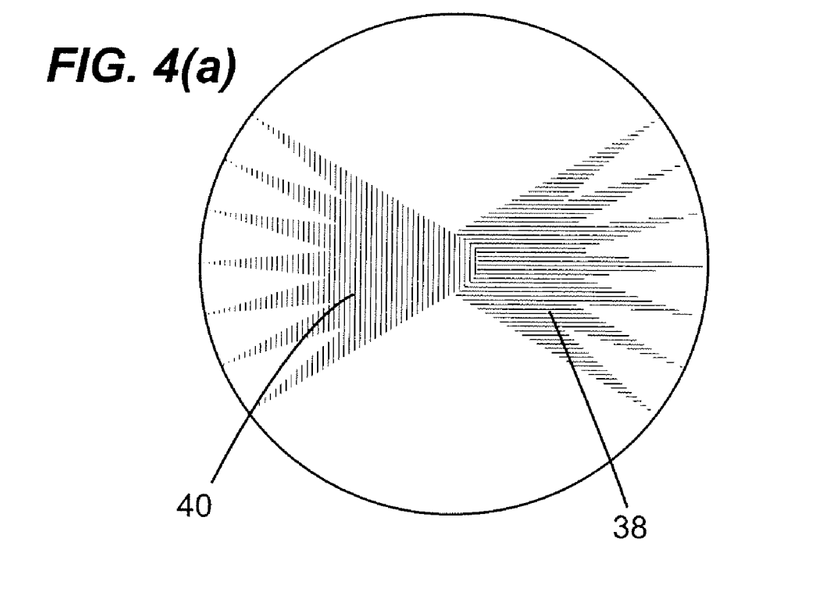
FIG. 4(a) is an illustration of the over-weighted and under-weighted regions that result from a series of super-short-scan reconstructions with different center angles.
Figure 4B:
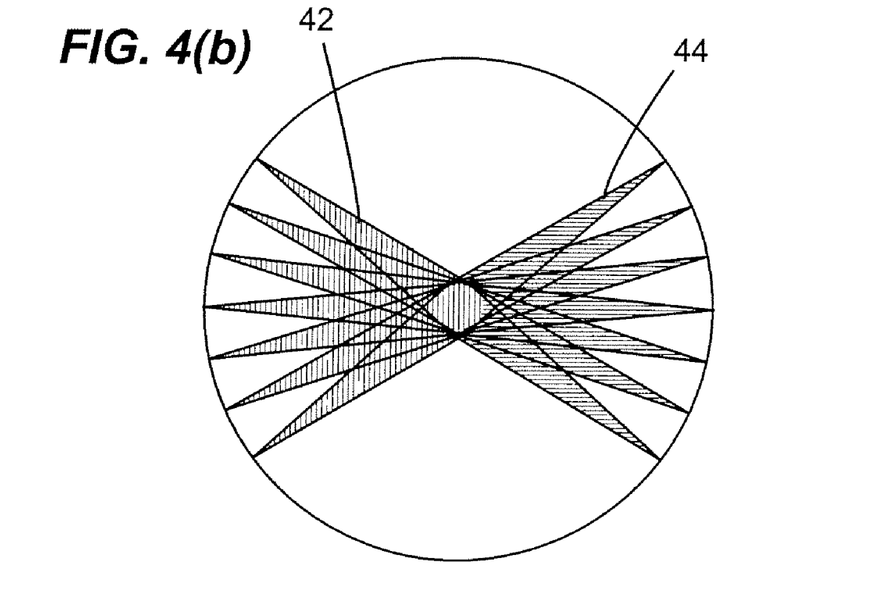
FIG. 4(b) is an illustration of the weight compensation that maybe achieved using a correction term as applied to the over-weighted and under-weighted regions shown in FIG. 4(a)

The mishandling of data that results from incorrectly weighting this wedge of data may also be applied in the case of a continuous view weight. This may be accomplished by first noting that the reconstruction process is a linear process and therefore, reconstruction with a particular view weight function F gives the same result as reconstructing many images (with view weight functions {f1, f2, f3, etc. . . . }) and averaging the resulting images, wherein the function F is the average of the view weight functions, f1, f2, f3, etc. For example, if an infinite series of reconstructions are performed with view weights equal to 1 in the interval [δ, 180+6] (and zero elsewhere) for all δ between −10 and +10, the result is identical to the result obtained by reconstructing with a view weight that ramps up linearly from 0 to 1 over the finite range of angles from −10 to +10 degrees and then ramps back to zero from +170 to +190 degrees. Since the Fourier transform is also linear, the net result in the Fourier Domain is the average of the Fourier Domain content of the individual reconstructions. It may be noted that, while the Fourier content of each reconstruction is similar to the central reconstruction, the "wedge" of mishandled data lies in the direction rotated by δ degrees, resulting in a spread of the over-weighted and under-weighted regions for over 20 degrees of longitude. At low latitudes this results in a weight that approaches one in both the over-weighted and under-weighted regions, while at high latitudes, the weight is still zero and two in the portions of the under and over weighted regions respectively. FIG. 4(a) illustrates the over-weighted and under-weighted regions that typically result from a series of super-short-scan reconstructions with different center angles. As may be observed from FIG. 4(a), the over-weighted regions are indicated by the reference numeral 38 and the under-weighted regions are indicated by the reference numeral 40. In order to compensate for these incorrectly weighted regions of Radon (Fourier) space, in accordance with one embodiment of the present invention, a correction term may further be applied, as will be described in greater detail below. FIG. 4(b) is an exemplary illustration of the weight compensation that maybe achieved using the correction term as applied to the over-weighted and under-weighted regions shown in FIG. 4(a). As may be observed in FIG. 4(b), the lines indicated by the reference numeral 44 are negatively weighted, while the lines indicated by the reference numeral 42 are positively weighted. As may be further noted, the weight compensation is essentially applied at the boundaries of the under-weighted or over-weighed regions. However, by the application of a continuous view weight, as described above, these lines are spread out resulting in effective weight compensation in these regions.

In order to reduce the presence of the over-weighted and the under-weighted data regions as described above, in one embodiment of the present invention, a method for reconstructing cone-beam projection data, acquired along a circular scan trajectory is disclosed. As will be discussed in greater detail below, the disclosed method comprises computing a weighting function and backprojecting a correction term for at least a subset of projection views, based upon the weighting function.

Figure 5:
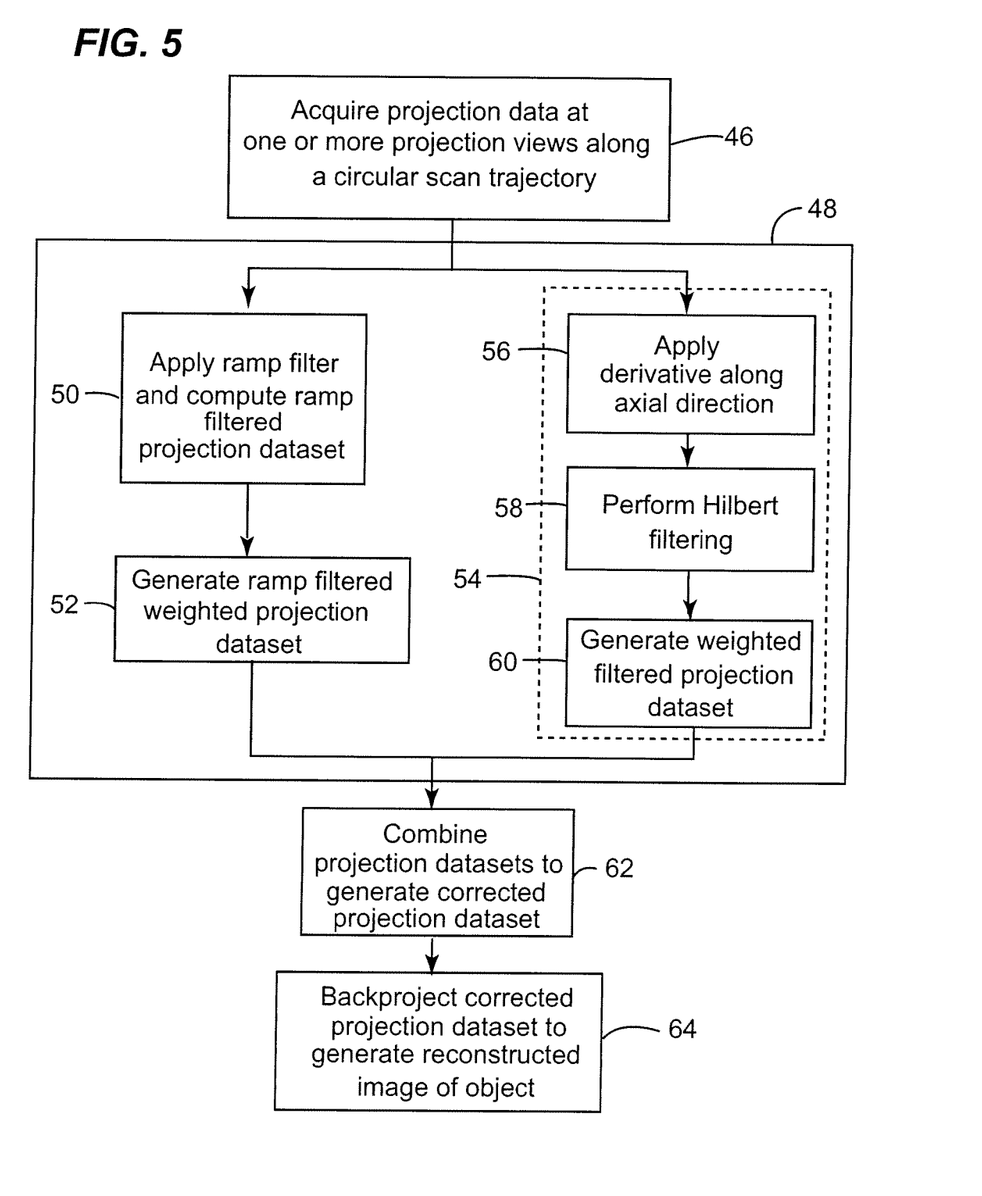
FIG. 5 is a flowchart illustrating exemplary steps for reconstructing cone-beam projection data, acquired along a circular scan trajectory, in accordance with one embodiment of the present invention.

Referring to FIG. 5 now, in step 46, projection data at one or more projection views, is acquired. In one embodiment, the projection data is acquired along a circular scan trajectory, using a CT system. In step 48, a corrected projection dataset is generated based upon a weighted derivative applied to at least a subset of the projection data. In one embodiment, the step of generating a corrected projection dataset further comprises computing a correction term in step 54, for at least a subset of the projection data. In a particular embodiment, the step 54 of computing a correction term further comprises applying a derivative to the subset of the projection data in step 56 and performing a Hilbert filtering of the subset of the projection data in step 58 to generate a filtered projection dataset. In one embodiment, the derivative is applied to the subset of the projection data in a direction parallel to the axis of rotation of the CT scanner and the Hilbert filtering is performed along one or more detector rows. The step 54 of computing the correction term further comprises applying a weight in step 60, based upon a weighting function, to generate a weighted filtered projection dataset. In one embodiment, the weighting function may be determined as a function of the detector row, the detector column and the view angle associated with each data point in the projection dataset. In a particular embodiment, the weighting function may be computed based upon a derivative of a view weight, with respect to a view angle. For example, for projection data acquired along a circular scan trajectory, an appropriate weighting function may be computed as shown in equation (1) below:

$$W(u,v,\lambda) = k\, D(\lambda) C(v) \qquad (1)$$

wherein k is a positive constant, $D(\lambda)$ is the derivative of a standard voxel weight with respect to a parallel view angle and $C(v)$ is the cone angle of a ray with coordinate v on the detector. For example, if the standard weight of a voxel is 0 from −180 degrees to −100 degrees, and then ramps up linearly to 1 at −80 degrees, and then is again constant at 1 until 80 degrees, and then ramps down linearly to 0 by 100 degrees) and then remains at zero for the remainder of the rotation (to 180 degrees), the value of $D(\lambda)$ is zero, except in the angular range between −100 and −80, and the angular range between 80 and 100. In these ranges, the value is, respectively, 1/20 and −1/20.

As mentioned above, the weighting function, in one embodiment, is computed based upon a derivative of the view weight, computed for one or more projection views. Further, in a particular embodiment, the derivative of the view weight is computed in a direction parallel to the axis of the scanner and the Hilbert filter is applied to the subset of the projection data, along one or more detector rows. In other words, the derivative is applied in a direction orthogonal to the tangent of the path of the x-ray source while the Hilbert transform is still applied tangent to the path of the x-ray source. Referring to FIG. 4(b) now, this results in the application of a negative weight in two of the quadrants of the Fourier space illustrated in FIG. 4(b). These two negatively weighted quadrants, (indicated by the lines 44 shown in FIG. 4(b)), reduce the over-weighting, while the other quadrants (those with positive weightings, as indicated by the lines 42 in FIG. 4(b)) augment the weighting in the underweighted regions. Further, when the derivative of the view weight is zero, the view weight remains constant, and the steps 56 and 58 of computing a derivative and applying a Hilbert transform respectively, need not be computed for view angles for which the derivative of the view weight is zero. The view weights may also be assigned a negative weight when the view weights decrease, thereby causing the quadrants with positive weights and negative weights to be switched. Further, since the thickness of the wedge of mishandled data is dependent on the cone-angle, in one embodiment, the view weight may be determined based upon one or more cone-angles associated with the projection views.

As may be further noted, the weighting function is zero for views at which the view weight is not changing, i.e., the derivative is zero, and hence for these views, the step 48 of generating a corrected projection dataset comprises generating a ramp filtered projection dataset, based on the acquired projection data. In one embodiment, the step of generating a ramp filtered projection dataset comprises applying a ramp filter to the acquired projection data and computing a ramp filtered projection dataset in step 50. In step 52, a weighting operation is applied to the ramp filtered projection dataset to generate a ramp filtered weighted projection dataset.

Referring to FIG. 5 again, the ramp filtered weighted projection dataset generated in step 52 and the correction term generated in step 54 are then combined together to generate the corrected projection dataset in step 62. In step 64, the corrected projection dataset is backprojected, along one or more projection views to generate a reconstructed image of the object.

Figure 6:
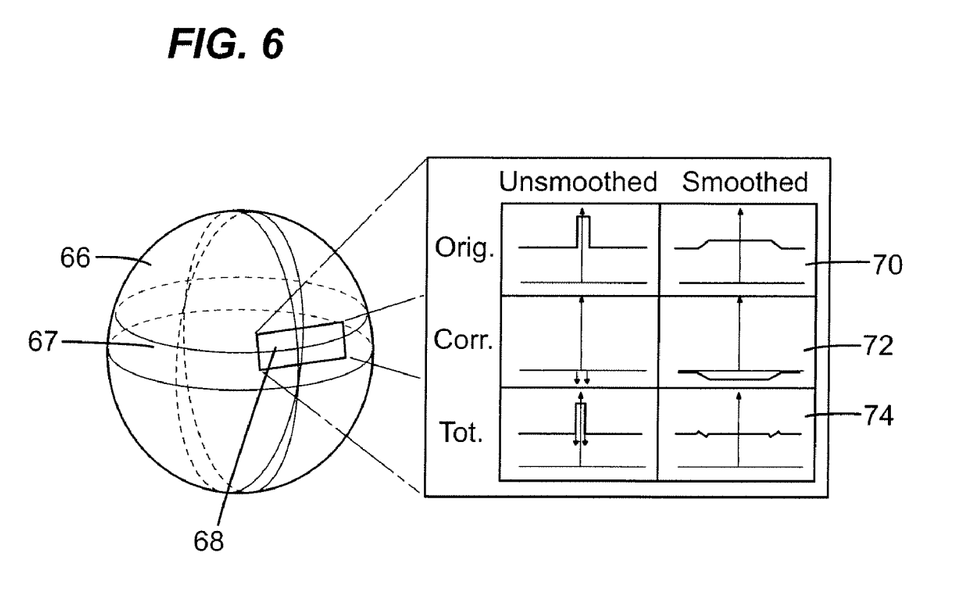
FIG. 6 is an illustration of the correction term spread over a view angle range that compensates for the over-weighted region of the Radon (Fourier) space on a single latitude line.

FIG. 6 is an exemplary illustration of how the spreading of the correction term over a view angle range compensates for the over-weighted region of the Radon (Fourier) space on a single latitude line. In the example shown in FIG. 6, the radon space weight function is plotted at different points on the surface of the sphere 66. In the particular example shown in FIG. 6, the plots 70, 72 and 74, illustrate the radon weight function on the latitude circle 67 in the region represented by the rectangular area 68, on the surface of the sphere 66 after smoothing in the view angle. At each point on the portion of the latitude circle 67 within this rectangular section, the radon weight function is plotted as a function of the longitude. The plot 70 illustrated in FIG. 6, is the original plot that corresponds to the case where a standard filtering of the projection data and a particular view weight is used to generate a ramp filtered weighted projection dataset; the plot 72 illustrates a correction plot that is obtained when a correction term is applied to the subset of projection data and the plot 74 illustrates the sum of the plots 70 and 72. This sum represents the radon weighting function that is obtained when the ramp filtered weighted projection dataset and the correction term are added together to generate the corrected projection data in a manner as described in detail, with respect to FIG. 5 above.

Figure 7:
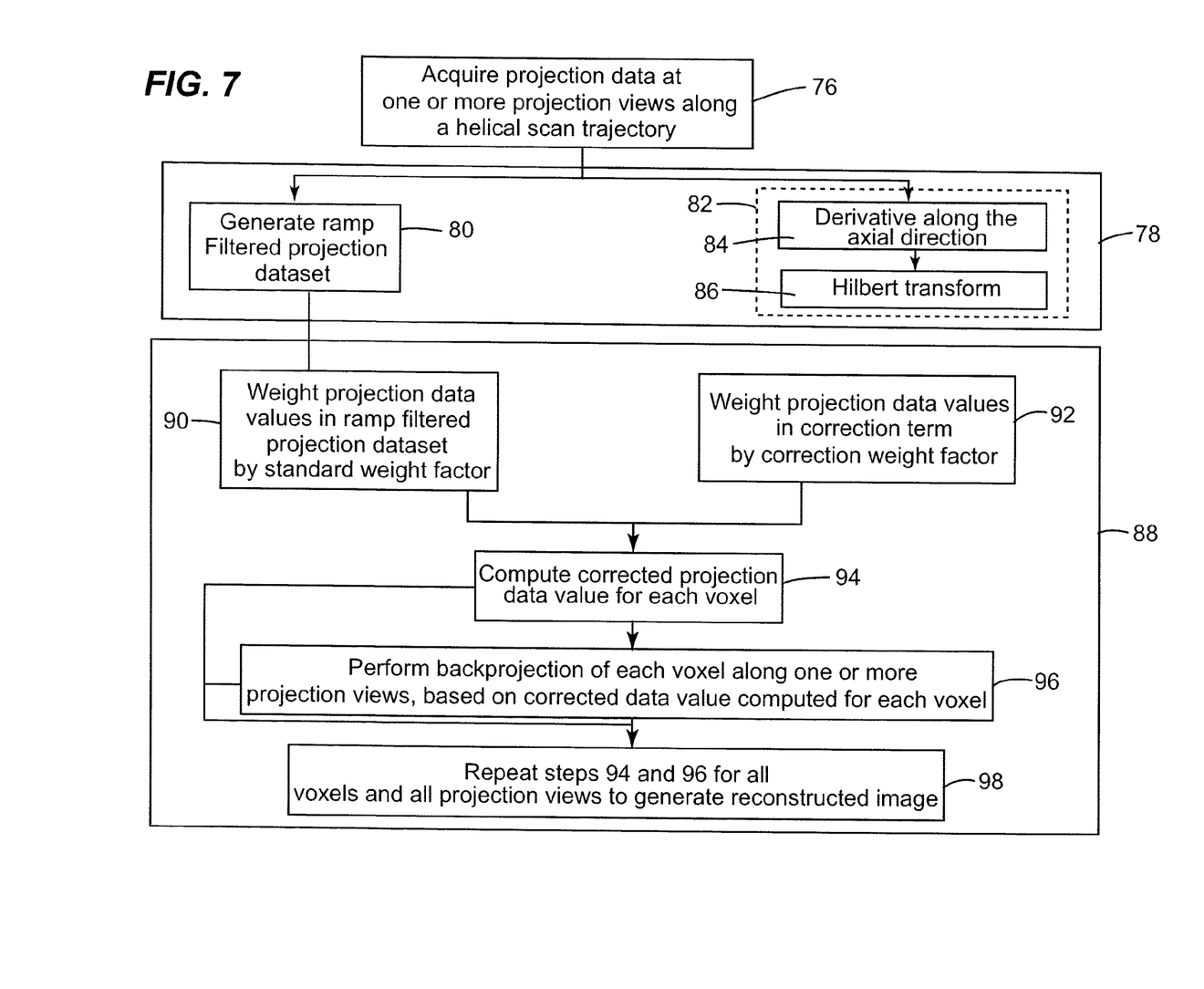
FIG. 7 is a flowchart illustrating exemplary steps for reconstructing cone-beam projection data acquired along a helical trajectory, in accordance with one embodiment of the present invention.

In another embodiment, a method for reconstructing cone-beam projection data, acquired along a helical trajectory is disclosed. FIG. 7 is a flowchart illustrating exemplary steps for reconstructing cone-beam projection data acquired along a helical trajectory, in accordance with one embodiment of the present invention. In step 76, projection data is acquired at one or more projection views, along a helical trajectory. In step 78, the projection data is processed to generate at least one of a ramp filtered projection dataset in step 80 and a correction term in step 82. In one embodiment, generating a ramp filtered projection dataset comprises applying a ramp filter, as described above. In one embodiment, the step 82 of generating a correction term comprises applying a derivative to a subset of the projection data in step 84 and performing a Hilbert filtering of the subset of the projection data in step 86 to generate a filtered projection dataset. As mentioned above, in one embodiment, the derivative is applied to the subset of the projection data in a direction parallel to the axis of rotation of the CT scanner and the Hilbert filter is applied along one or more detector rows.

In step 88, the ramp filtered projection dataset computed in step 80 and the correction term computed step 82 are backprojected along one or more projection views to generate a reconstructed image of the object. In one embodiment, the step 88 of performing the backprojection comprises computing a corrected projection data value for the backprojection of each voxel, along each projection view. In a particular embodiment, the corrected data value for a voxel is computed by weighting one or more projection data values comprising the ramp filtered projection dataset using a standard weight factor computed in step 90 and weighting one or more projection data values comprising the correction term using a correction weight factor computed in step 92. In step 96, a backprojection of each voxel along a projection view is performed based on the corrected data value computed for each voxel in step 94, to generate the reconstructed image volume. As may be noted, the step 94 of computing a corrected data value and the step 96 of performing a backprojection of a voxel is repeated for all projection views and all voxels comprising the image volume (as indicated by step 98, shown in FIG. 7), wherein an updated corrected data value is computed for each voxel at each step of the backprojection, to generate the reconstructed image.

In one embodiment, the standard weight factor corresponds to a weighting function that is determined as a function of the detector row, the detector column, the view angle associated with each projection view and the position of the voxel along the projection ray. Further, for projection data acquired along a helical trajectory, the wedge of data that is mishandled is not directly dependent on the cone angle, but rather on the mismatch between the cone angles of the various forward and conjugate rays. The correction weight factor, in this case, is therefore computed by considering the various cone angles of these rays and the various values of the partial derivatives of the standard weight factor computed for the projection rays. In one embodiment, the standard weight factor is computed by choosing the standard view weights for any voxel at a series of view angles separated by 180 degrees such that their sum is equal to one. As a result of this normalization condition, the sum of the partial derivatives of the standard view weight at these angles must be zero. Therefore, the correction weight for a given voxel at a given view angle may be derived by forming a series of uniformly weighted segments each with an angular range of 180 degrees such that the difference between the weights applied to consecutive segments is equal to the partial derivative of the view weight at that location and the view weight outside the backprojection range is zero. The size of the wedges of data that are mishandled may then be used to indicate the correction weight that may be applied.

In accordance with one embodiment of the present invention, the correction weight factor to be applied to a voxel, for example, when it projects onto the boundary of a Tam window for a high pitch helical scan, may be computed as follows. When the partial derivative of the view weight at a corresponding view angle is nonzero (for example, it has a value d), there is only one other view that needs to be considered. At this view, the partial derivative of the view weight is equal to −d. A backprojection over the interval that connects these two views does not produce a wedge of mishandled frequencies since the line that connects the source positions corresponding to the endpoints of this range is a π-line containing the point. Even though some mishandled frequencies exist, they do not form a wedge; rather, they are confined to the polar frequency region. The correction weight factor in this case is zero in spite of the non-zero cone angle and the non-zero derivative of the view weight.

Figure 8:
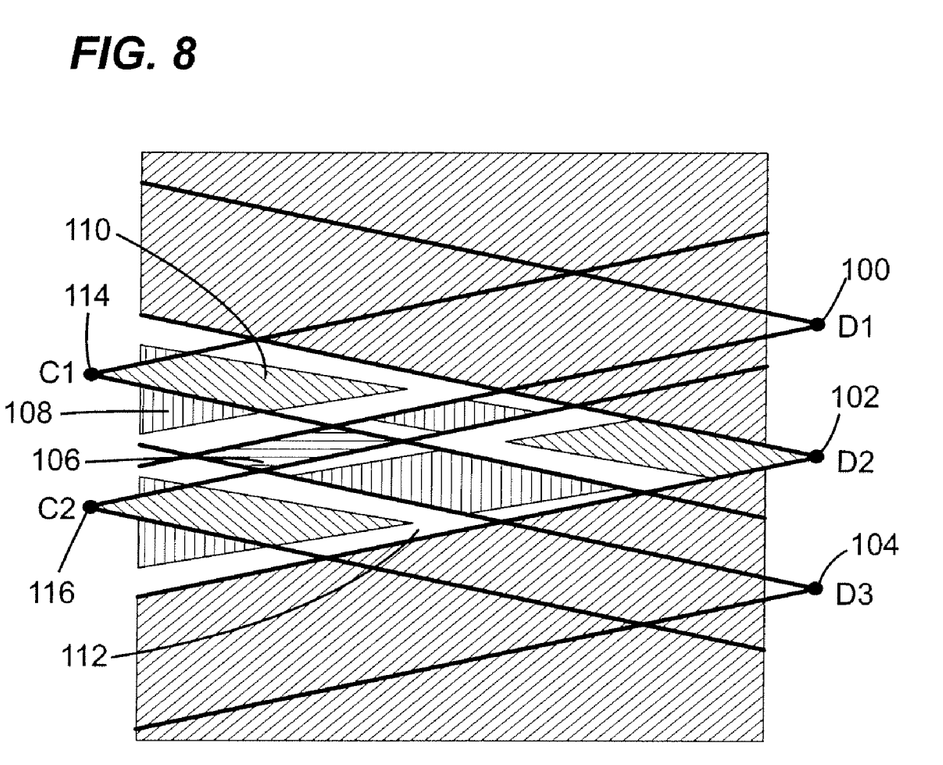
FIG. 8 is an illustration of the computation of the correction weight factor for reconstructing cone-beam projection data, acquired along a helical trajectory.

FIG. 8 is an illustration of the computation of the correction weight factor in accordance with one embodiment of the present invention. Referring to FIG. 8, a cross section through a helix that contains the voxel or point of interest that is parallel to the rays at the parallel view angle is illustrated. The weight that should be applied to the correction term generated at the view labeled D2 (represented by the reference numeral 102) is computed as follows. The voxels that are projected onto the detector at the view labeled D2 represent the total number of visible views. The voxels within the region represented by the reference numeral 106 have a redundancy of 1, while the voxels in the regions represented by the reference numerals 108 and 110 have redundancies of two and three respectively. In one embodiment, the points of interest in the regions labeled by the reference numerals, 106, 108 and 110 may be weighted by the reciprocal of the redundancy for the standard view weight (since, and as mentioned above, the correction weight factor depends on the partial derivative of the standard weight factor). More specifically, the points in the regions labeled by the reference numerals, 106, 108 and 110 are seen from exactly one, two, and three views respectively and are weighted by 1, ½, and ⅓, respectively. The projection of a voxel or a point near the top or bottom boundary of the detector receives a weight that is somewhere between the discrete values of 1, ½, and ⅓ so that the standard weight for a given voxel is continuous in a given view angle. Further, for points of interest that lie in the regions labeled by the reference numerals, 106, 108 and 110, the correction term is weighted by zero since the derivative of the view weight is zero, in this case.

Referring to FIG. 8 again, a point that lies inside the transition region 112 is seen from all the three views, namely, C2, D2 and C1, represented by the reference numerals, 116, 102 and 114 respectively. However, at view C1, this point is not easily seen so it is given a lower weight at this view than it is at the other views. The trajectory of the point travels downward, until it leaves the volume that is seen by C1 and enters the region 108. At this point, the view weight is zero from C1, ½ from C2, and ½ from D2. Conversely, for another view angle, this point falls in the region indicated by the reference numeral 110 and can be seen by C1, C2, and D2. Accordingly, this point is weighted by ⅓ from each of these views. From the above discussion, in one example, the view weights for the views shown in FIG. 8 may reasonably be as follows: 0.14 from view C2 with a derivative of −0.4, 0.43 from view C1 with a derivative of 0.2, and 0.43 from view D2 with a derivative of 0.2. It may be noted that the sum of the view weights is equal to one and that the sum of the derivatives is equal to zero due to the normalization condition. Considering a trajectory with a piecewise constant weight that is zero except for in the segments connecting the helix points C1, D2, and C2, the weight in these sections is determined by cumulatively adding the derivatives as mentioned above. In one example, the section from C2 to D2 is given a weight of 0.2 since this is the derivative at C2 while the section from D2 to C1 is given a weight of 0.4 since this is the sum of the derivatives at C2 and D2.

Figure 9:
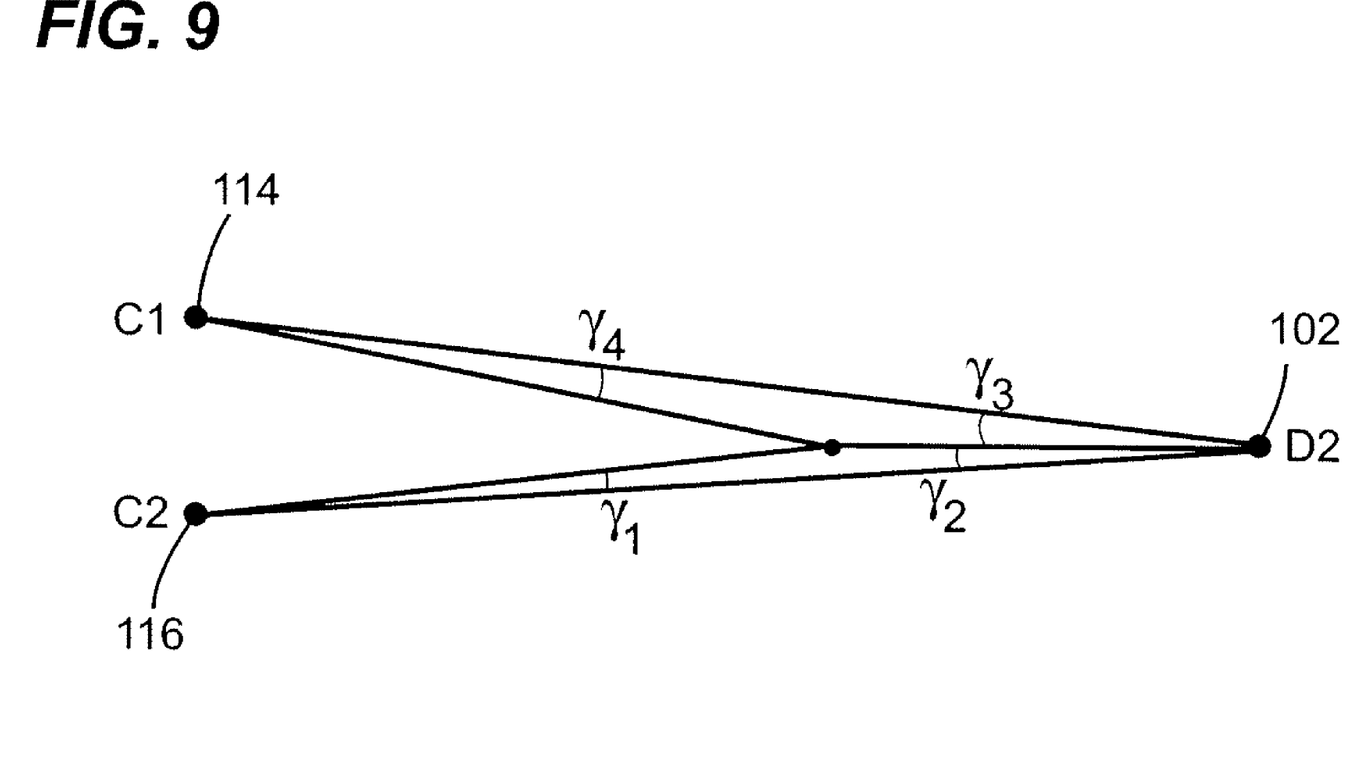
FIG. 9 is an illustration of the computation of the correction weight factor for reconstructing cone-beam projection data, acquired along a helical trajectory, in greater detail.

It may further be noted that this pattern may be followed to show that the proper weight for the portion of the trajectory above C1 is zero since this is the sum of the derivative at C2, D2, and C1 (0.2+0.2−0.4=0). The size of the wedge of mishandled data for each of these trajectory segments may be derived as follows. If the vector pointing from the initial point of the segment toward the reconstruction point is represented by $\alpha_i$ and the vector pointing from the final point of the segment towards the reconstruction point is represented by $\alpha_f$, the wedge of mishandled data will disappear if these two vectors exactly oppose each other (i.e., if $\alpha_i = -\alpha_f$). In fact, the angular size of the wedge will be equal to the angle between $\alpha_i$ and $-\alpha_f$. It may further be noted that this angle can either be split in half in order to assign the compensation weight needed at each endpoint or a separate angle may be computed for each endpoint (a forward angle and a backward angle) wherein these two angles add up to the correct value. An example of the latter approach is to compare $\alpha_i$ and $-\alpha_f$ to the ray that connects the two endpoints. The forward angle may be multiplied by the segment view weight to produce the compensation weight at the initial point. The backward angle may be multiplied by the negative of the segment view weight to produce the compensation weight at the final point. FIG. 9 illustrates the computation of the correction weights in greater detail. Referring to FIG. 13, the correction weight factor at C2 is given by $\gamma_1(0.2)$, the weight at D2 is given by $\gamma_2(-0.2)+\gamma_3(0.4)$ and the weight at C1 is given by $\gamma_4(-0.4)$.

As may be noted from FIG. 9, that since $\gamma_1$ and $\gamma_2$ are positive while $\gamma_3$ and $\gamma_4$ are negative, the weight at C1 and C2 will be positive while the weight at D2 will be negative. However, since the Hilbert transform is taken in the opposite direction for the conjugate views, the sign of the correction term in the Fourier domain remains the same for all views.

Figure 10:
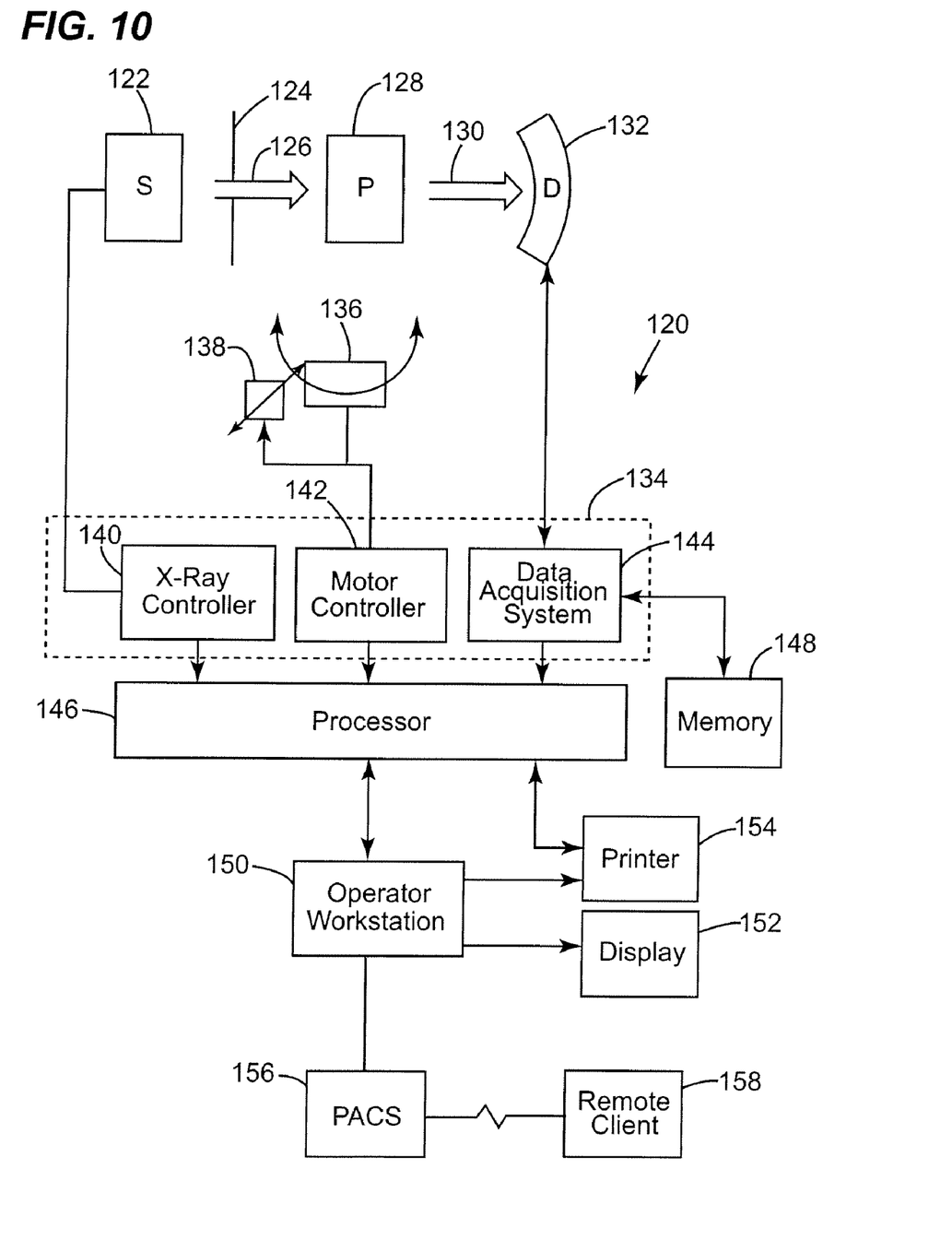
FIG. 10 is an illustration of an imaging system for generating an image of an object, in accordance with one embodiment of the invention.

In another embodiment of the present invention, an imaging system for generating an image of an object is disclosed. FIG. 10 is an illustration of an imaging system for generating an image of an object in accordance with one embodiment of the invention. In a particular embodiment, the imaging system 120 is a computed tomography (CT) system designed to acquire original image data, process the image data for generating an image of the object and display the image data. As illustrated in FIG. 1, the imaging system 120 includes a source of x-ray radiation 122 positioned adjacent to a collimator 124. In one embodiment, the x-ray radiation source 122 may be an x-ray tube.

Referring to FIG. 10, collimator 124 permits a stream of radiation 126 to pass into a region in which an object, for example, a subject of interest 128 is positioned. A portion of the radiation 130 passes through or around the subject and impacts a detector array, represented generally at reference numeral 132. Detector elements of the array produce electrical signals that represent the intensity of the incident x-ray beam. These signals are acquired and processed to reconstruct images of the features within the subject 128. Source 122 is controlled by a system controller 134, which furnishes both power, and control signals for CT examination sequences. Moreover, detector 132 is coupled to the system controller 134, which commands acquisition of the signals generated in the detector 132. The system controller 134 may also execute various signal processing and filtration functions, such as for initial adjustment of dynamic ranges, interleaving of digital image data, and so forth. In general, system controller 134 commands operation of the imaging system to execute examination protocols and to process acquired data. In the present context, system controller 134 also includes signal processing circuitry, typically based upon a general purpose or application-specific digital computer, associated memory circuitry for storing programs and routines executed by the computer, as well as configuration parameters and image data, interface circuits, and so forth.

System controller 134 is coupled to a rotational subsystem 136 and a linear positioning subsystem 138. The rotational subsystem 136 enables the x-ray source 122, collimator 124 and the detector 132 to be rotated one or multiple turns around the subject 128. It should be noted that the rotational subsystem 136 might include a gantry. Thus, the system controller 134 may be utilized to operate the gantry. The linear positioning subsystem 138 enables the subject 128, or more specifically a table, to be displaced linearly. Thus, the table may be linearly moved within the gantry to generate images of particular areas of the subject 128. Additionally, as will be appreciated by those skilled in the art, the source of radiation may be controlled by an x-ray controller 140 disposed within the system controller 134. Particularly, the x-ray controller 140 is configured to provide power and timing signals to the x-ray source 122. A motor controller 142 may be utilized to control the movement of the rotational subsystem 136 and the linear positioning subsystem 138. Further, the system controller 134 is also illustrated comprising a data acquisition system 144. In this exemplary embodiment, the detector 132 is coupled to the system controller 134, and more particularly to the data acquisition system 144. The data acquisition system 144 receives data collected by readout electronics of the detector 132. The data acquisition system 144 typically receives sampled analog signals from the detector 132 and converts the data to digital signals for subsequent processing by a processor 146. The processor 146 is typically coupled to the system controller 134. The data collected by the data acquisition system 144 may be transmitted to the processor 146 and moreover, to a memory 148. It should be understood that any type of memory to store a large amount of data might be utilized by such an exemplary system 120. Moreover, the memory 148 may be located at this acquisition system or may include remote components for storing data, processing parameters, and routines described below.

In one embodiment, the imaging system 120 is configured to acquire projection data along a circular scan trajectory, at one or more projection views. In a particular embodiment, the processor 146 is configured to process the plurality of electrical signals from the detector 132 to generate the projection data. The processor 146 is further configured to generate a corrected projection dataset based upon a weighted derivative applied to a subset of the projection data. The processor 146 is then configured to backproject the corrected projection dataset along one or more projection rays associated with one or more of the projection views, to generate a reconstructed image of the object. In another embodiment, the imaging system 120 is configured to acquire projection data along a helical scan trajectory. In a particular embodiment, the processor 146 is configured to process the plurality of electrical signals from the detector 132 to generate the projection data. The processor 146 is further configured to process the projection data to generate a ramp filtered projection dataset and a correction term, compute a corrected data value for a voxel, wherein the corrected data value for each voxel is computed based on weighting one or more projection data values comprising the ramp filtered projection dataset and the correction term by at least one of a standard weight factor or a correction weight factor. The processor 146 is then configured to perform a backprojection of the corrected data value computed for the voxel to generate a reconstructed image of the object, wherein the step of computing the corrected data value and the step of performing the backprojection is repeated for each voxel and along each projection view, to generate the reconstructed image of the object.

Referring to FIG. 10 again, the processor 146 is further configured to receive commands and scanning parameters from an operator via an operator workstation 150 typically equipped with a keyboard and other input devices. An operator may control the system 120 via the input devices. Thus, the operator may observe the reconstructed image and other data relevant to the system from processor 146, initiate imaging, and so forth. A display 152 coupled to the operator workstation 150 may be utilized to observe the reconstructed image and to control imaging. Additionally, the scanned image may also be printed by a printer 154 which may be coupled to the operator workstation 150. The display 152 and printer 154 may also be connected to the processor 146, either directly or via the operator workstation 150. Further, the operator workstation 150 may also be coupled to a picture archiving and communications system (PACS) 156. It should be noted that PACS 156 might be coupled to a remote client 158, radiology department information (RIS), hospital information system (HIS) or to an internal or external network, so that others at different locations may gain access to the image and to the image data.

It should be further noted that the processor 146 and operator workstation 150 may be coupled to other output devices, which may include standard, or special purpose computer monitors and associated processing circuitry. One or more operator workstations 150 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Embodiments of the present invention disclose efficient techniques for reconstructing cone-beam projection data acquired along circular and helical scan trajectories. The disclosed embodiments have several advantages including the ability to generate images with low cone-beam artifact levels and low noise levels, while still achieving desired image quality characteristics, such as, high computational efficiency, good dose usage and resistance to motion artifacts.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for generating an image of an object, the method comprising:
    acquiring projection data at one or more projection views, wherein the projection data is acquired along a circular scan trajectory;
    generating a corrected projection dataset by:
        computing a correction term for a subset of the projection data to generate a weighted filtered projection dataset corresponding to the subset;
        for a remainder of the projection data, applying a ramp filter to the remainder of the projection data and weighting the ramp filtered remainder of the projection data to generate a ramp filtered weighted projection dataset;
    combining the weighted filtered projection dataset and the ramp filtered weighted projection dataset to generate a corrected projection dataset; and
    backprojecting the corrected projection dataset along one or more projection rays associated with one or more of the projection views, to generate a reconstructed image of the object.

2. The method of claim 1, wherein generating the correction term comprises applying a derivative to the subset of the projection data.

3. The method of claim 1, wherein computing the correction term comprises applying a derivative to at least the subset of the projection data, and performing a Hilbert filtering of the subset of the projection data to generate a filtered projection dataset.

4. The method of claim 3, wherein the derivative is applied to at least the subset of the projection data in a direction parallel to the axis of rotation of a CT scanner.

5. The method of claim 3, wherein the Hilbert filtering of the subset of the projection data is performed along one or more detector rows.

6. The method of claim 3, wherein computing the correction term further comprises weighting the filtered projection dataset based upon a derivative of a view weight, computed for one or more of the projection views.

7. The method of claim 6, wherein the filtered projection dataset is further weighted based on one or more cone angles associated with one or more of the projection views.

8. The method of claim 1, wherein the projection data comprises cone-beam projection data.

9. A method for generating an image of an object, the method comprising:
    acquiring projection data at one or more projection views, wherein the projection data is acquired along a helical scan trajectory;
    processing the projection data by:
        computing a correction term for a subset of the projection data to generate a filtered projection dataset corresponding to the subset;
        for a remainder of the projection data, applying a ramp filter to the remainder of the projection data and weighting the ramp filtered remainder of the projection data to generate a ramp filtered projection dataset;
    computing a corrected projection data value for each voxel by weighting one or more projection data values of the ramp filtered projection dataset using a standard weight factor and weighting one or more projection data values of the filtered projection dataset using a correction weight factor; and performing a backprojection of the corrected data value computed for each voxel to generate a reconstructed image of the object.

10. The method of claim 9, wherein computing the correction term comprises applying a derivative to the subset of the projection data and performing a Hilbert filtering of the subset of the projection data to generate the filtered projection dataset.

11. The method of claim 10, wherein the derivative is applied to at least the subset of the projection data in a direction that is substantially parallel to the axis of rotation of a CT scanner.

12. The method of claim 10, wherein the Hilbert filtering of the subset of the projection data is performed along one or more detector rows.

13. The method of claim 9, wherein the standard weight factor is computed as a function of at least one of a detector row, a detector column, the view angle associated with each projection view and the position of each voxel along a projection ray.

14. The method of claim 9, wherein the correction weight factor is computed based on computing at least one of a cone angle associated with a projection ray and one or more data values of the partial derivatives of the standard weight factor computed for the projection rays.

15. The method of claim 9, wherein the projection data is acquired using a computed tomography (CT) system.

16. The method of claim 9, wherein the projection data comprises cone-beam projection data.

17. A computed tomography (CT) system for generating an image of an object, the system comprising:
   an x-ray source configured to project an x-ray beam from a plurality of positions through the object;
   a detector configured to produce a plurality of electrical signals corresponding to the x-ray beam; and
   a processor configured to process the plurality of electrical signals to generate projection data, to compute a correction term for a subset of the projection data to generate a weighted filtered projection dataset corresponding to the subset, to apply a ramp filter to a remainder of the projection data and weight the ramp filtered remainder of the projection data to generate a ramp filtered weighted projection dataset, to combine the weighted filtered projection dataset and the ramp filtered weighted projection dataset to generate a corrected projection dataset, and to backproject the corrected projection dataset along one or more projection rays associated with one or more of the projection views, to generate a reconstructed image of the object, wherein the projection data is acquired along a circular scan trajectory, along one or more projection views.

18. A computed tomography (CT) system for generating an image of an object, the system comprising:
   an x-ray source configured to project an x-ray beam from a plurality of positions through the object;
   a detector configured to produce a plurality of electrical signals corresponding to the x-ray beam; and
   a processor configured to process the plurality of electrical signals to generate projection data, to compute a correction term for a subset of the projection data to generate a filtered projection dataset corresponding to the subset; to apply a ramp filter to a remainder of the projection data and weight the ramp filtered remainder of the projection data to generate a ramp filtered projection dataset, to compute a corrected projection data value for each voxel by weighting one or more projection data values of the ramp filtered projection dataset using a standard weight factor and weighting one or more projection data values of the filtered projection dataset using a correction weight factor, to perform a backprojection of the corrected data value computed for each voxel to generate a reconstructed image of the object, wherein the projection data is acquired along a helical scan trajectory, along one or more projection views.

* * * * *

UNITED STATES PATENT AND TRADEMARK OFFICE
CERTIFICATE OF CORRECTION

PATENT NO.          : 7,792,238 B2                                                      Page 1 of 1
APPLICATION NO. : 12/032810
DATED                   : September 7, 2010
INVENTOR(S)         : Pack It is certified that error appears in the above-identified patent and that said Letters Patent is hereby corrected as shown below:

In Column 4, Line 47, delete "180+6]" and insert -- 180+$\delta$] --, therefor.

Signed and Sealed this

Second Day of November, 2010

David J. Kappos
*Director of the United States Patent and Trademark Office*